United States Patent [19]

Saito et al.

[11] 4,110,440

[45] Aug. 29, 1978

[54] PESTICIDAL ORGANOPHOSPHORIC ACID ESTER ANHYDRIDES

[75] Inventors: Junichi Saito, Tokyo; Akio Kudamatsu, Kanagawa; Toyohiko Kume, Tokyo; Kozo Shiokawa, Kanagawa; Shinichi Tsuboi, Tokyo, all of Japan

[73] Assignee: Nihon Tokushu Noyaku Seizo K.K., Tokyo, Japan

[21] Appl. No.: 848,415

[22] Filed: Nov. 3, 1977

[30] Foreign Application Priority Data

Nov. 5, 1976 [JP] Japan .................................. 51/132478

[51] Int. Cl.$^2$ .......................... A01N 9/36; C07F 9/165
[52] U.S. Cl. .................................... 424/207; 260/933
[58] Field of Search .......................... 260/933; 424/207

[56] References Cited

FOREIGN PATENT DOCUMENTS 1,450,400 7/1966 France ..................................... 260/933

Primary Examiner—Anton H. Sutto
Attorney, Agent, or Firm—Burgess, Dinklage & Sprung

[57] ABSTRACT

Organophosphoric acid ester anhydrides of the formula

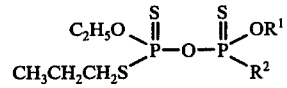

in which
$R^1$ is alkyl with 1-6 carbon atoms, and
$R^2$ is alkoxy, alkylthio, alkylamino or dialkylamino
which possess arthropodicidal and nematicidal properties.

11 Claims, No Drawings

PESTICIDAL ORGANOPHOSPHORIC ACID ESTER ANHYDRIDES

The present invention relates to and has for its objects the provision of particular new organophosphoric acid ester anhydrides which possess arthropodicidal and nematicidal properties, active compositions in the form of mixtures of such compounds with solid and liquid dispersible carrier vehicles, and methods for producing such compounds and for using such compounds in a new way especially for combating pests, e.g. arthropods and nematodes, with other and further objects becoming apparent from a study of the within specification and accompanying examples.

French Patent Specification No. 1,450,400 discloses that the organophosphorus compounds of the general formula

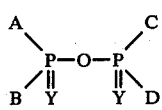
(VI), in which

A, B, C and D each represent alkyl, alkoxy or alkylthio, and

Y represents oxygen, sulphur or selenium, have an insecticidal activity.

Furthermore, the long-term use of large amounts of organophosphorus compounds, such as Parathion, EPN, BAYCID and Sumithion, organochlorine compounds, such as BHC and DDT, and carbamate compounds, such as Sevin, is bringing about the deplorable phenomenon that the pests are attaining resistance to these chemicals.

Hence there is a need for new pesticides which have only a low toxicity to warm-blooded animals but which are effective against those pests that have attained resistance to prior-art pesticides.

The present invention now provides, as new compounds, the organophosphoric acid ester anhydrides of the general formula

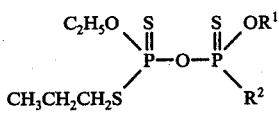
(I)

in which $R^1$ represents alkyl with 1–6 carbon atoms, and $R^2$ represents alkoxy, alkylthio, alkylamino or dialkylamino.

It has been found that compounds of the formula (I) exhibit unusually strong insecticidal, acaricidal and nematicidal activities, and possess a higher effectiveness and a wider controlling effect than compounds of the formula (VI); particularly, they have an excellent activity against spider mites that have attained resistance to various known organophosphorus pesticides.

Preferably, $R^1$ represents alkyl with 1–4 carbon atoms (especially methyl or ethyl) and $R^2$ represents alkoxy, alkylthio, alkylamino or dialkylamino with 1–6 (especially 1–4) carbon atoms in the or each alkyl group. Especially preferred $R^2$ radicals are those in which the or each alkyl group is selected from methyl, ethyl, n-propyl, isopropyl and sec.-butyl groups.

The present invention also provides a process for the preparation of a compound of the formula (I), in which (a) a dithiophosphoryl halide of the general formula

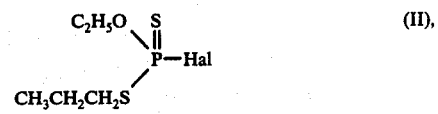
(II), in which

Hal represents halogen, preferably chlorine, is reacted with a salt of an organophosphoric acid ester of the general formula

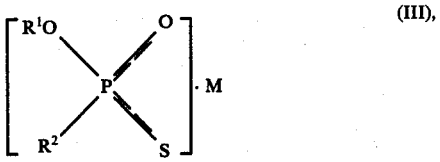
(III), in which $R^1$ and $R^2$ have the meanings stated above, and

M represents an alkali metal (preferably sodium or potassium) or ammonium, or (b) a thio- or amidothio-phosphoryl halide of the general formula

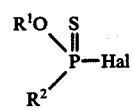
(IV), in which $R^1$ and $R^2$ have the meanings stated above, and

Hal represents halogen, preferably chlorine, is reacted with an O-ethyl-S-n-propylphosphorodithioate of the general formula

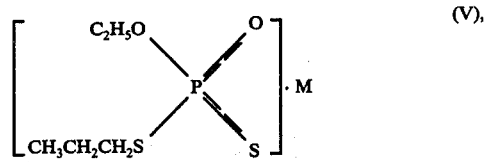
(V), in which

M represents an alkali metal (especially potassium or sodium) or ammonium.

The compounds of the general formula (III) can be synthesized by the method indicated in the following equation:

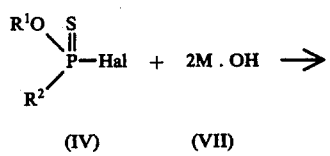

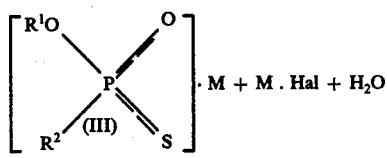

wherein $R^1$, $R^2$ and M have the meanings stated above.

An example of the dithiophosphoryl halides of the general formula (II) is O-ethyl-S-n-propyldithiophosphoryl chloride.

Examples of the salts of the organophosphoric acid esters of the general formula (III) are sodium O,O-diethylphosphorothioate, sodium O-ethyl-S-propylphosphorodithioate, sodium O-ethyl-N-isopropylphosphoroamidothioate, sodium O-ethyl-N,N-diethylphosphoroamidothioate, sodium O-ethyl-N-sec.-butylphosphoroamidothioate, and sodium O,O-dimethyl phosphorothioate, and the corresponding potassium salts and ammonium salts.

Examples of the halides of the general formula (IV) are O,O-diethylthiophosphoryl chloride, O-ethyl-S-n-propyldithiophosphoryl chloride, O-ethyl-N-isopropylamidothiophosphoryl chloride, O-ethyl-N,N-diethylamidothiophosphoryl chloride, O-ethyl-N-sec.-butylamidothiophosphoryl chloride, and O,O-dimethylthiophosphoryl chloride.

Examples of the salts of the general formula (V) are sodium O-ethyl-S-n-propyldithiophosphate, potassium O-ethyl-S-n-propyldithiophosphate and ammonium O-ethyl-S-n-propyldithiophosphate.

Examples of the compounds of the general formula (VII) are sodium hydroxide, potassium hydroxide, and ammonium hydroxide.

The course of process variant (e) may be illustrated by the following equations:

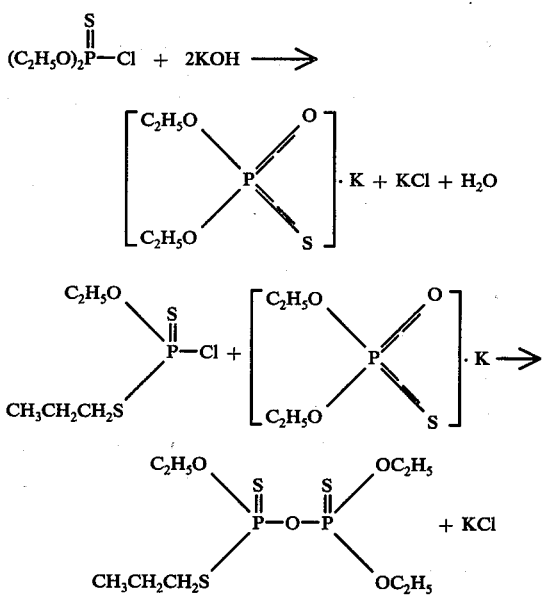

The course of process variant (b) can be illustrated by the following equation:

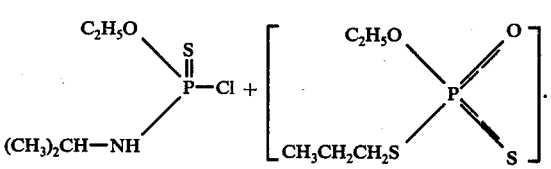

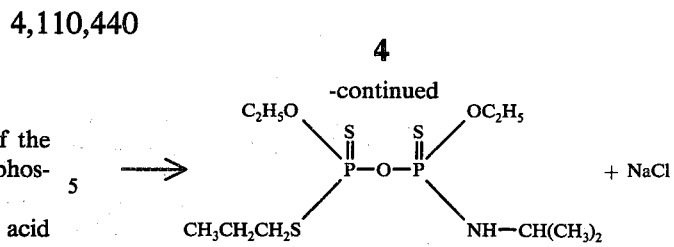

Process variants (a) and (b) of the present invention are carried out preferably using a solvent or diluent. Examples of such solvents or diluents are water and inert organic solvents selected from aliphatic, alicyclic and aromatic hydrocarbons (which optionally may be chlorinated), such as hexane, cyclohexane, petroleum ether, ligroin, benzene, toluene, xylene, methylene chloride, chloroform, carbon tetrachloride, ethylene chloride, trichloroethylene and chlorobenzene; ethers, such as diethyl ether, methyl ethyl ether, diisopropyl ether, dibutyl ether, propylene oxide, dioxane and tetrahydrofuran; ketones, such as acetone, methyl ethyl ketone, methyl isopropyl ketone and methyl isobutyl ketone; nitriles, such as acetonitrile, propionitrile and acrylonitrile; alcohols, such as methanol, ethanol, isopropanol, tert.-butanol and ethylene glycol; esters, such as ethyl acetate and amyl acetate; acid amides such as dimethyl formamide and dimethyl acetamide; sulfones and sulfoxides, such as dimethyl sulfoxide and dimethyl sulfone; and bases, such as pyridine.

Process variants (a) and (b) of the present invention can be performed in a wide temperature range. In general, the process is carried out at a temperature between −20° C. and the boiling point of the mixture, preferably at a temperature of from 0° to 100° C. Furthermore, the reaction is carried out at atmospheric pressure, although it can also be performed under an elevated or reduced pressure.

Also, the reaction in the preparative process of the present invention can be effected in the presence of an acid binder. Examples of acid binders are the customary hydroxides, carbonates, bicarbonates and alcoholates of alkali metals, and tertiary amines such as triethylamine, diethylaniline or pyridine.

As already mentioned, the compounds according to the present invention are distinguished by an excellent insecticidal, acaricidal and nematicidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine since they are also active against animal parasites, in particular ectoparasites such as parasitic fly larvae, arachnids, ticks and nematodes.

The active compounds are well tolerated by plants, have a favorable level of toxicity to warm-blooded animals, and can be used for combating arthropod pests, especially insects and acarids, and nematode pests, which are encountered in agriculture, in forestry, in the protection of stored products and of materials, and in the hygiene field. They are active against normally sensitive and resistant species and against all or some stages of development. The abovementioned pests include:

from the class of the *Isopoda*, for example *Oniscus asellus*, *Armadillidium vulgare* and *Porcellio scaber;* from the class of the *Diplopoda*, for example *Blaniulus guttulatus;* from the class of the *Chilopoda*, for example *Geophilus carpophagus* and *Scutigera* spec.;

from the class of the *Symphyla*, for example *Scutigerella immaculata;* from the order of the *Thysanura*, for example *Lepisma saccharina;* from the order of the *Collembola*, for example *Onychiurus armatus;* from the order of the *Orthoptera*, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the *Dermaptera*, for example *Forficula auricularia;* from the order of the *Isoptera*, for example *Reticulitermes* spp.;

from the order of the *Anoplura*, for example *Phylloxera vastatrix, Pemphigus* spp., *Pediculus humanus corporis, Haematopinus* spp. and *Linognathus* spp.;

from the order of the *Mallophaga*, for example *Trichodectes* spp. and *Damalinea* spp.;

from the order of the *Thysanoptera*, for example *Hercinothrips femoralis* and *Thrips tabaci;* from the order of the *Heteroptera*, for example *Eurygaster* spp., *Dysdercus intermedius, Piesma quadrata, Cimex lectularius, Rhodnius prolixus* and *Triatoma* spp.;

from the order of the *Homoptera*, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the *Hymenoptera*, for example *Diprion* spp., *Hoplocampa* spp., *Lasius* spp., *Monomorium pharaonis* and *Vespa* spp.;

from the order of the *Diptera*, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the *Siphonaptera*, for example *Xenopsylla cheopis* and *Ceratophyllus* spp.;

from the class of the *Arachnida*, for example *Scorpio maurus* and *Latrodectus mactans;* from the order of the *Acarina*, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The plant-parasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp., and *Trichodorus* spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant-protection agents, such as other arthropodicides and nematicides, or fungicides, bactericides, rodenticides, herbicides, fertilizers, growth-regulating agents, growth promoters, plant nutrients, agents for improving soil structure, bird repellents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–20% and preferably 0.005–10%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods and nematodes, which comprises applying to at least one of correspondingly (a) such acarids, (b) such nematodes, and (c) the corresponding habitat thereof, i.e. the locus to be protected, e.g. to a growing crop, to an area where a crop is to be grown, to plant seeds or to a domestic animal, a correspondingly combative or toxic amount, i.e. an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The following preparative examples illustrate the process according to the present invention:

EXAMPLE 1

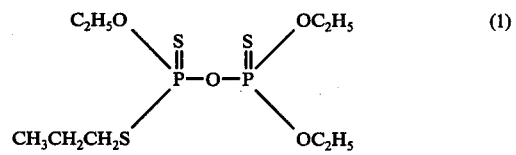

(1)

26 g of potassium O-ethyl S-n-propyldithiophosphate and 18.9 g of O,O-diethylthiophosphoryl chloride were added to 50 ml of acetonitrile. After the mixture had been stirred at 80° C. for 5 hours, it was poured into 300 ml of ice-water and then extracted by the addition of 100 ml of toluene. The extract was washed first with a 2% aqueous sodium carbonate solution and then with water, dried with anhydrous sodium sulfate and thereafter distilled to remove toluene. Distillation under reduced pressure gave 26.2 g of the mixed anhydride of (O-ethyl-S-propylphosphorodithioate) and (O,O-diethylphosphorothioate) as the final product. Boiling point = 140°–142° C./0.5 mm Hg; $n_D^{20}$ = 1.5098.

EXAMPLE 2

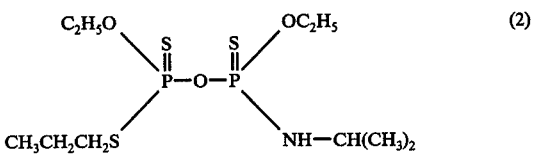

A mixture of 22.6 g of O-ethyl-N-isopropylamidothiophosphate and 21.9 g of O-ethyl-S-n-propylthiophosphoryl chloride in 50 ml of acetonitrile was reacted and worked up in a manner analogous to that of Example 1 to give 25.5 g of the mixed anhydride of (O-ethyl-S-n-propylphosphorodithioate) and (O-ethyl-N-isopropylphosphorothionoamidate) as the final product. Boiling point = 160°–161° C./0.6 mm Hg; $n_D^{20}$ =0 1.5200.

The compounds in the following table were prepared by methods analogous to those of Examples 1 and 2.

EXAMPLE 5

A dusting agent was prepared by pulverizing and mixing 2 parts of compound No. 2 and 98 parts of a mixture (1:3) of talc and clay. This could be applied by scattering.

EXAMPLE 6

A dusting agent was prepared by pulverizing and mixing 1.5 parts of compound No. 4, 0.5 part of isopropyl hydrogen phosphate (PAP), and 98 parts of a mixture (1:3) of talc and clay.

EXAMPLE 7

10 parts of compound No. 5, 10 parts of bentonite, 78 parts of a mixture (1:3) of talc and clay, and 2 parts of lignin sulfonate were mixed. 25 parts of water were added to the mixture. The whole was mixed thoroughly and then processed with an extrusion granulator into granules of 20 to 40 mesh, which were dried at 40°–50° C.

EXAMPLE 8

95 parts of clay powder having a particle size distribution of 0.2 to 2 mm were placed in a rotary mixer. During rotation, there were sprayed over the particles 5 parts of a solution of compound No. 6 in an organic solvent, thereby wetting them uniformly. The, drying at Table 1

$$\underset{\underset{CH_3CH_2CH_2S}{}}{\overset{C_2H_5O}{\diagdown}}\overset{S}{\underset{\|}{P}}-O-\overset{S}{\underset{\|}{P}}\overset{OR^1}{\diagup}_{R^2} \quad (I)$$

| Compound No. | $R^1$ | $R^2$ | Physical constants b.p./mmHg | $n_D^{20}$ |
|---|---|---|---|---|
| 3 | $C_2H_5-$ | $CH_3(CH_2)_2S-$ | 160 – 161° C/0.6 mmHg | 1.5390 |
| 4 | $C_2H_5-$ | $C_2H_5\diagdown N- \diagup C_2H_5$ | 158 – 160° C/0.5 mmHg | 1.5190 |
| 5 | $C_2H_5-$ | $C_2H_5CH-NH \atop \| \atop CH_3$ | 156 – 158° C/0.55 mmHg | 1.5154 |
| 6 | $CH_3$ | $CH_3O-$ | 132 – 135° C/0.5 mmHg | 1.5246 |

Various pesticidal compositions according to this invention are described in the following Examples. The compounds of the present invention are each identified by the numbers from the preparative examples. Parts are by weight.

EXAMPLE 3

A wettable powder was prepared by pulverizing and mixing 15 parts of compound No. 1, 80 parts of a mixture (1:5) of diatomaceous earth and kaolin, and 5 parts of an emulsifier (a polyoxyethylene alkylphenyl ether). This could be diluted with water to a concentration of 0.05% before application by spraying.

EXAMPLE 4

An emulsifiable concentrate was prepared by mixing and stirring 30 parts of compound No. 2, 30 parts of xylene, 30 parts of methylnaphthalene and 10 parts of a polyoxyethylene alkylphenyl ether. This could be diluted with water to a concentration of 0.05% before spraying.

40° to 50° C. was effected in order to form granules.

EXAMPLE 9

An oil preparation was prepared by mixing and stirring 0.5 part of compound No. 6, 20 parts of a high-boiling aromatic compound and 79.5 parts of kerosine.

The pesticidal activity of the compounds of this invention is illustrated by the following biotest examples wherein the compounds according to the present invention are each identified by the number (given in brackets) from the preparative examples hereinabove and the known comparison compound is:

(A) = 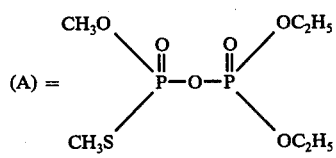

(disclosed in French Patent Specification No. 1,450,400)

EXAMPLE 10

Test on larvae of *Prodenia litura Fabricius*
Solvent: xylene, 3 parts by weight
Emulsifier: polyoxyethylene alkylphenyl ether, 1 part by weight To form a suitable preparation of the active compound, 1 part by weight of the active compound was mixed with the above amount of the solvent containing the above amount of the emulsifier, and the mixture was diluted with water to a predetermined concentration.

Sweet-potato leaves were dipped in an aqueous preparation, of a predetermined concentration, of the active compound. After drying in the air, the leaves were placed in a Petri dish 9 cm in diameter. Then 10 third-instar larvae of *Prodenia litura Fabricius* were placed in the Petri dish. The dish was placed in a constant-temperature room at 28° C. Twenty-four hours later, the number of dead larvae was determined in order to calculate the kill ratio. The results are shown in Table 2

Table 2

| Compound No. | Kill ratio (%) at a concentration of active compound (ppm) of | |
|---|---|---|
| | 1000 | 100 |
| (1) | 100 | 100 |
| (2) | 100 | 100 |
| (3) | 100 | — |
| (4) | 100 | — |
| (5) | 100 | 100 |
| (6) | 100 | — |
| (A) | 0 | 0 |

EXAMPLE 11

Test on *Callosobruchus chinensis*

The bottom of a Petri dish 9 cm in diameter was covered with a filter paper, onto which was placed 1 ml of an aqueous preparation, at a predetermined concentration, of the active compound (prepared as in Example 10). 20 *Callosobruchus chiensis* beetles were placed therein, and the Petri dish was allowed to stand in a constant-temperature room at 28° C. for 24 hours. After 24 hours had elapsed, the number of dead beetles was determined in order to calculate the kill ratio. The results are shown in Table 3

Table 3

| Compound No. | Kill ratio (%) at a concentration of active compound (ppm) of | | |
|---|---|---|---|
| | 1000 | 100 | 10 |
| (1) | 100 | 100 | 100 |
| (2) | 100 | 100 | 100 |
| (3) | 100 | 100 | 100 |
| (4) | 100 | 100 | 100 |
| (5) | 100 | 100 | 100 |
| (6) | 100 | 100 | 100 |
| (A) | 100 | 0 | 0 |

EXAMPLE 12

Test on *Nephotettix cincticeps* (Resistant to organophosphorus chemicals)

Rice plants each about 10 cm in grass height were planted in pots each 12 cm in diameter. On to the rice plants there was applied an aqueous preparation, at a predetermined concentration, of the active compound (prepared as in Example 10 at a rate of 10 ml per pot. After drying the applied preparation, wire-gauze cages each 7 cm in diameter and 14 cm in height were placed over the pots, into which cages 30 female imagos of *Nephotettix cincticeps* were released. The pots were then placed in a constant-temperature room, and 24 hours later, the number of dead insects was determined in order to calculate the kill ratio. The results are shown in Table 4.

Table 4

| Active compound | Kill ratio (%) at concentration of active compound (ppm) of | |
|---|---|---|
| | 1000 | 100 |
| (1) | 100 | 100 |
| (2) | 100 | 100 |
| (3) | 100 | 100 |
| (6) | 100 | 100 |
| (A) | 30 | — |

EXAMPLE 13

Test on larvae of *Culex pipiens pallens Coquillett*

100 ml of an aqueous preparation having a predetermined concentration of the active compound were placed in a tall-sided Petri dish 9 cm in diameter. Into the dish were released 25 larvae (4th instar) of *Culex pipiens pallens Coquillett*, and then the dish was placed in a constant-temperature room at 28° C. Twenty-four hours later, the number of dead larvae was determined in order to calculate the kill ratio. The results are shown in Table 5.

Table 5

| Active compound | Kill ratio (%) at a concentration of active compound (ppm) of | | |
|---|---|---|---|
| | 1 | 0.1 | 0.01 |
| (1) | 100 | 100 | 100 |
| (2) | 100 | 100 | — |
| (3) | 100 | 100 | — |
| (5) | 100 | 100 | — |
| (6) | 100 | 100 | — |
| (A) | 20 | 0 | 0 |

EXAMPLE 14

Test on *Musca domestica vicina*

A filter paper was laid on the bottom of a Petri dish 9 cm in diameter, and 1 ml of an aqueous preparation having a predetermined concentration of the active compound (as prepared in Example 10) was poured into the dish. 10 female imagos of *Musca vicina* were introduced therein. Then, the dish was placed in a constant-temperature room at 28° C. Twenty-four hours later, the number of killed imagos was determined in order to calculate the kill ratio. The results are shown in Table 6.

Table 6

| Compound No. | Kill ratio (%) at a concentration of active compound (ppm) of |
|---|---|
| | 1000 |
| (1) | 100 |
| (2) | 100 |
| (3) | 100 |
| (4) | 100 |
| (6) | 100 |
| (A) | 0 |

EXAMPLE 15

Test on *Blattella germanica*

The bottom of a Petri dish 9 cm in diameter was covered with a filter paper, onto which was placed 1 ml of an aqueous preparation having a predetermined concentration of the active compound(prepared as in Example 10). 10 imagos of *Blattella germanica* were placed therein, and the Petri dish was allowed to stand in a constant-temperature room at 28° C. After 24 hours had elapsed the number of dead imagos was determined in order to calculate the kill ratio. The results are shown in Table 7.

Table 7

| Active compound | Kill ratio (%) at a concentration of active compound (ppm) of | |
|---|---|---|
| | 1000 | 100 |
| (1) | 100 | 100 |
| (3) | 100 | 100 |
| (6) | 100 | 100 |
| (A) | 0 | 0 |

EXAMPLE 16

Test on the mite *Tetranychus telarius* (Spray test)

The leaves of kidney bean plants in the two-leaf stage were infested with 50 to 60 larvae of *Tetranychus telarius*. The kidney bean plants were cultivated in pots each 9 cm in diameter. Two days after the infestation, an aqueous preparation, at a predetermined concentration, of the active compound (formulated as in Example 10) was sprayed over the leaves at a rate of 20 ml per pot. Then, the pots were put in a greenhouse. 10 days later, the acaricidal effect was evaluated and expressed on the following scale:

3 = 0% survival of the mites
2 = not more than 5% survival
1 = more than 5% survival up to 50% survival
0 = more than 50% survival The results are shown in Table 8.

Table 8

| Compound No. | Control effect at a concentration of active ingredient (ppm) of | | |
|---|---|---|---|
| | 1000 | 300 | 100 |
| (1) | 3 | 3 | 3 |
| (2) | 3 | 3 | — |
| (3) | 3 | 3 | — |
| (4) | 3 | 3 | — |
| (5) | 3 | 3 | 3 |
| (6) | 3 | 3 | 3 |
| (A) | 0 | 0 | 0 |

EXAMPLE 17

Test on *Meloidogyne incognita acrita*

An active-compound preparation was prepared by pulverizing and mixing 2 parts by weight of the active compound and 98 parts by weight of talc.

The active compound processed as above was added to soil infested by *Meloidogyne incognita acrita* in such amounts as to give a concentration of 50 ppm, 25 ppm, 10 ppm and 5 ppm, respectively. The mixture was stirred and mixed uniformly and then charged into pots each of 0.0002 are. In the treated soil were sown about 20 seeds of tomato (variety: KURIHARA) per pot. The tomato seeds were cultivated in a greenhouse. Four weeks later, the grown roots were withdrawn without damaging them, and the degree of injury of 10 roots out of them was evaluated based on the following ratings to determine a root-knot index:

Degree of injury
0 — no root-knot formation (perfect control)
1 — slight root-knot formation
3 — much root-knot formation
4 — most root-knot formation (corresponding to non-treatment)

$$\text{Root-knot index} = \frac{\Sigma \text{ (rating} \times \text{number of roots)}}{\text{(total number of)} \times 4 \text{ (examined roots)}} \times 100$$

From the above, the following control effect was obtained:

$$\text{Control effect} = \frac{\text{(root-knot index)} - \text{(root-knot index)}}{\text{root-knot index of untreated plot}} \times 100$$

A control effect of 100% means a perfect control. The results are shown in Table 9

Table 9

| Active compound | Control effect (%) at a concentration of active compound (ppm) of | |
|---|---|---|
| | 50 | 25 |
| (1) | 100 | — |
| (3) | 100 | 100 |
| (6) | 100 | — |
| (A) | 0 | 0 |

It will be appreciated that the instant specification and examples are set forth by way of illustration and not limitation, and that various modifications and changes may be made without departing from the spirit and scope of the present invention.

What is claimed is:

1. An organophosphoric acid ester anhydride of the formula

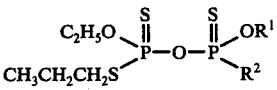

in which
R$^1$ is alkyl with 1–6 carbon atoms, and
R$^2$ is alkoxy, alkylthio, alkylamino or dialkylamino.

2. A method of combating arthropods or nematodes, or to a habitat thereof, an arthropodicidally or nematicidally effective amount of a compound according to claim 1.

3. The method according to claim 2, wherein such compound is the mixed anhydride of
   (O-ethyl-S-propylphosphorodithioate) and
   (O,O-diethylphosphorothioate),
   (O-ethyl-S-propylphosphorodithioate) and
   (O-ethyl-S-propylphosphorodithioate),
   (O-ethyl-S-propylphosphorodithioate) and
   (O-ethyl-N-isopropylphosphorothionoamidate),
   (O-ethyl-S-propylphosphorodithioate) and
   (O-ethyl-N,N-diethylphosphorothionoamidate),
   (O-ethyl-S-propylphosphorodithioate) and
   (O-ethyl-N-sec.-butylphosphorothionoamidate), or
   (O-ethyl-S-propylphosphorodithioate) and
   (O,O-dimethylphosphorothioate).

4. An arthropodicidal or nematicidal composition containing as active ingredient an arthropodicidally or nematicidally effective amount of a compound according to claim 1 in admixture with a diluent.

5. A compound according to claim 1, in which R$^1$ is alkyl with 1–4 carbon atoms and R$^2$ is alkoxy, alkylthio, alkylamino or dialkylamino with 1 to 6 carbon atoms in each alkyl group.

6. A compound according to claim 1, wherein such compound is the mixed anhydride of (O-ethyl-S-propylphosphorodithioate) and (O,O-diethylphosphorothioate) of the formula

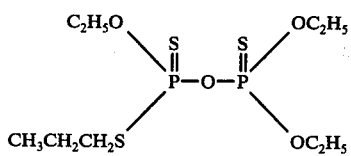

7. A compound according to claim 1, wherein such compound is the mixed anhydride of (O-ethyl-S-propylphosphorodithioate) and (O-ethyl-S-propylphosphorodithioate) of the formula

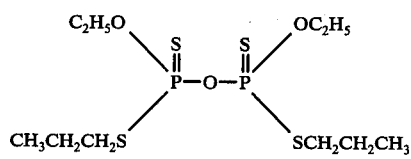

8. A compound according to claim 1, wherein such compound is the mixed anhydride of (O-ethyl-S-propylphosphorodithioate) and (O-ethyl-N-isopropylphosphorothionoamidate) of the formula

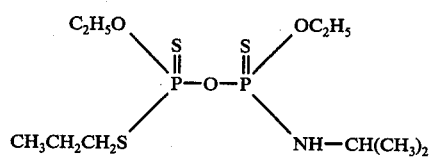

9. A compound according to claim 1, wherein such compound is the mixed anhydride of (O-ethyl-S-propylphosphorodithioate) and (O-ethyl-N,N-diethylphosphorothionoamidate) of the formula

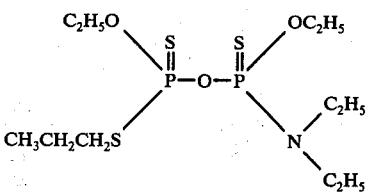

10. A compound according to claim 1, wherein such compound is the mixed anhydride of (O-ethyl-S-propylphosphorodithioate) and (O-ethyl-N-sec.-butylphosphorothionoamidate) of the formula

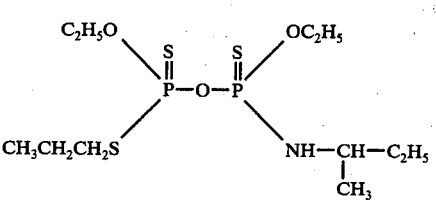

11. A compound according to claim 1, wherein such compound is the mixed anhydride of (O-ethyl-S-propylphosphorodithioate) and (O,O-dimethylphosphorothioate) of the formula

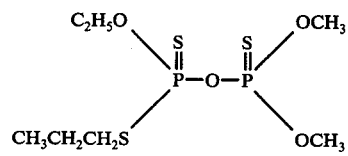

* * * * *